United States Patent
Bagaoisan et al.

(10) Patent No.: US 11,872,362 B2
(45) Date of Patent: Jan. 16, 2024

(54) REGROOMABLE BALLOON CATHETER SYSTEM AND METHODS OF USE

(71) Applicant: Lamamed, LLC, Hayward, CA (US)

(72) Inventors: Celso J. Bagaoisan, Union City, CA (US); Suresh S. Pai, Los Altos, CA (US); Scott R. Sershen, Foster City, CA (US)

(73) Assignee: Lamamed, LLC, Hayward, CA (US)

( * ) Notice: Subject to any disclaimer, the term of this patent is extended or adjusted under 35 U.S.C. 154(b) by 1079 days.

(21) Appl. No.: 16/612,707

(22) PCT Filed: Jun. 12, 2018

(86) PCT No.: PCT/US2018/037145
§ 371 (c)(1),
(2) Date: Nov. 11, 2019

(87) PCT Pub. No.: WO2018/231857
PCT Pub. Date: Dec. 20, 2018

(65) Prior Publication Data
US 2020/0206483 A1   Jul. 2, 2020

Related U.S. Application Data

(60) Provisional application No. 62/518,450, filed on Jun. 12, 2017.

(51) Int. Cl.
*A61M 25/10* (2013.01)
*A61M 25/00* (2006.01)
*A61L 29/08* (2006.01)

(52) U.S. Cl.
CPC .... *A61M 25/1038* (2013.01); *A61M 25/0097* (2013.01); *A61M 25/1002* (2013.01);
(Continued)

(58) Field of Classification Search
CPC .......... A61M 25/1038; A61M 25/0097; A61M 25/1002; A61M 2025/1004;
(Continued)

(56) References Cited

U.S. PATENT DOCUMENTS

| 5,623,940 A | 4/1997 | Daikuzono |
| 2009/0018500 A1 * | 1/2009 | Carter ................... A61M 25/10 604/99.01 |

(Continued)

FOREIGN PATENT DOCUMENTS

EP  2470253  * 4/2016

*Primary Examiner* — Theodore J Stigell
(74) *Attorney, Agent, or Firm* — Edward J. Baba; Bozicevic, Field & Francis LLP

(57) ABSTRACT

The various embodiments of the subject invention included herein provide devices, systems and methods for aiding the regrooming or refolding of balloons upon deflation. The scope of the inventions in this specification includes methods and devices that reduce the profile of balloons after deflation, reduce or eliminate wings, high-points, irregularities, bunching, thickening, and the like, and facilitate passage of a deflated balloon through a body void or lumen, or through a medical device such as a guide catheter, guide sheath, femoral or radial introducer sheath, and the like.

30 Claims, 8 Drawing Sheets

(52) U.S. Cl.
CPC .... *A61L 29/085* (2013.01); *A61M 2025/0008* (2013.01); *A61M 2025/1004* (2013.01); *A61M 2025/1079* (2013.01)

(58) Field of Classification Search
CPC .. A61M 2025/0008; A61M 2025/1079; A61M 25/10184
See application file for complete search history.

(56) References Cited

U.S. PATENT DOCUMENTS

| | | |
|---|---|---|
| 2014/0018732 A1 | 1/2014 | Bagaoisan et al. |
| 2014/0276532 A1 | 9/2014 | Zook et al. |

* cited by examiner

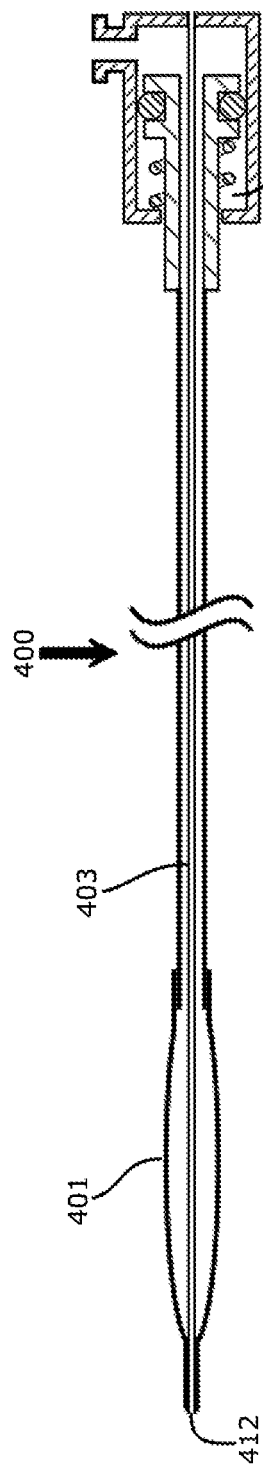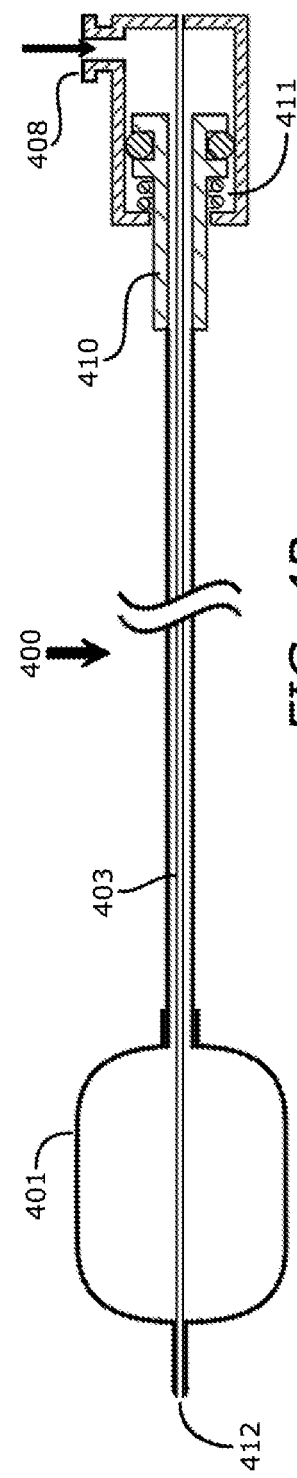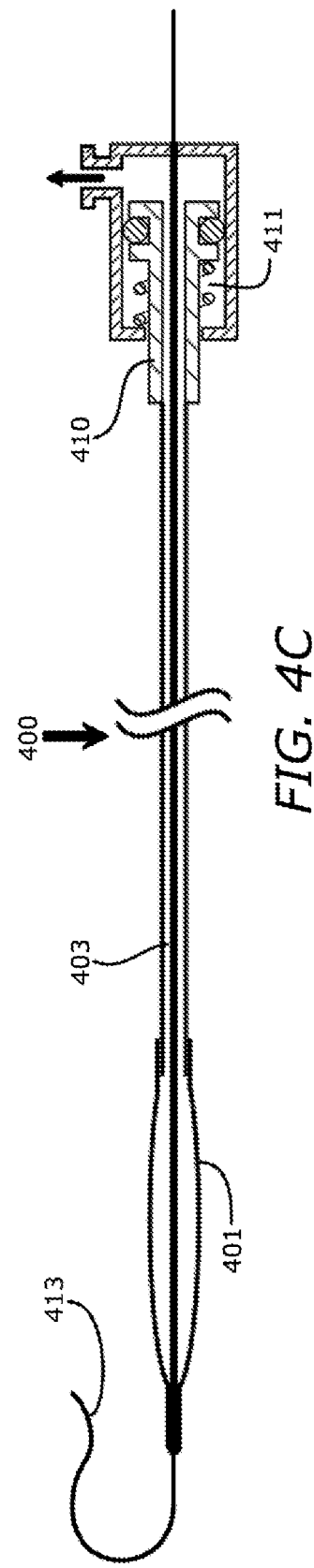

REGROOMABLE BALLOON CATHETER SYSTEM AND METHODS OF USE

CROSS-REFERENCE

This application claims the benefit of U.S. Provisional Patent Application No. 62/518,450 filed Jul. 12, 2017, which application is incorporated herein by reference in its entirety.

FIELD OF THE INVENTION

The field of the present invention relates generally to medical devices and methods and more specifically to expandable balloon dilatation catheter devices and methods for aiding the refolding or regrooming of during deflation of the balloon catheter devices. The devices and methods disclosed in this invention may also be applied to aid in the refolding or regrooming of other expandable members (e.g. braids, stent delivery systems, etc.).

BACKGROUND

It is common in medical procedures that employ dilatation-balloon types to expand the balloon multiple times often and different places in the anatomy peri-procedurally. For example, in cardiology balloons that are used to carry stents to the diseased target artery are first deployed to anchor the stent over the lesion and then subsequently deflated and re-expanded to post dilate the stent at a higher applied pressure. Another example would be during renal artery interventions where the same balloon may be used for angioplasty or dilatation of both renal arteries if disease or stenoses are encountered bilaterally. In other medical fields such as otolaryngology, emerging techniques like high pressure dilatation of the sinuses is often used to dilate multiple sinus ostia with the same device as a matter of practicality and sheer economics. Efficacy and safety are the primary demands in these procedures and the re-use of the dilatation balloons needs to be completed efficiently and without introduction of undesirable clinical sequelae in spite of multiple cycles of inflation, deflation and manipulation into and out of guide catheters and similar accessories in the peri-procedural setting. Most all contemporary balloons used in cardiology, peripheral vascular intervention and other medical procedures (e.g. kyphoplasty, balloon dilatation of the sinuses) are fabricated using processes where the balloon is pleated and folded to provide a neatly groomed low profile configuration. The low profile is based on a frequently desired clinical need for these types of balloon devices to traverse or cross narrow or restricted lumens. In the vascular setting, the restriction or luminal narrowing is typically due to atherosclerotic plaques, thrombus and the like. In otolaryngology, the restrictions in sinuses are usually due to physical anatomic restrictions and chronic rhinosinusitis.

A low cross sectional dimension or profile is also helpful to advance the balloon through the lumens of typically used guide catheters and sheaths and the like. After the initial inflation of current semi-compliant and non-compliant balloons using typical media (e.g. saline, saline contrast mixtures, air etc), these balloons often fail to return to a low profile upon deflation and tend to form wings as the media is removed from the balloon with vacuum pressure. In some medical procedures, the current practice is to manually re-groom to a lower working profile (i.e. a substantially collapsed state and small cross sectional dimension) to facilitate multiple utilizations during the same procedure.

For example, the instruction for use for the Relieva Solo™ and Relieva Solo Pro™ made by Acclarent (Acclarent IFU 005049 Revision A) instructs the operator to place three fingers equally centered on the sinus balloon to serve as a guide to form the wings during balloon deflation. Once the wings are formed, the instructions require gently re-wrapping the wings of the sinus balloon back around the catheter in a clockwise motion while patting the sinus balloon from the distal to proximal end without twisting the elongate catheter shaft. Once this is complete, the user is instructed to slide a protective sheath back over the balloon to restore the balloon to a tight profile and the balloon is now finally ready for re-use. These complex instructions highlight the cumbersome nature of what is required to prepare current devices for re-use and underscore the procedural delays associated with using these balloons in multiple dilatations in the same surgical setting.

It is also imperative that the balloon assumes a reasonably low profile to ensure safe retrieval back into the guide catheter or the like (if used) after deflation. At the end of many of these procedures, the guide catheter and/or guidewire used for accessing the target anatomy are left in place and only the balloon device is removed to enable imaging (e.g. selective angiography to assess a result in vascular procedures), lavage, aspiration, or flushing with saline or medications or the like. Typically the guide catheter is held stable while the balloon device is slowly retracted through its lumen. Guide catheters typically used in these different medical procedures (e.g. stenting, angioplasty, sinus dilatation etc) often have soft atraumatic tips which can easily invert and occupy some of the guide's luminal space and thereby sharply increasing the force required for removal of instruments the inner lumen and the end of a procedure. Thus it is obvious that a balloon that fails to assume a substantially low profile after deflation is not preferred as it could interfere with smooth passage through a guide catheter's tip and into its lumen. In this scenario, a physician could inadvertently apply a retraction force so high that the balloon or some component of the balloon (e.g. the distal) tip detaches from the balloon device and embolizes into the body of the patient potentially leading to catastrophic clinical outcomes.

Another other issue with the winging or ungroomed state relates to dislodging, damaging or adversely altering a deployed stent. In cases where the balloon forms wings (i.e. flats along the pleat/fold lines) during deflation and this winging occurs within the lumen of a stent, risks can be significant as the stent implant itself may be embolized or damaged to the extent that its clinical functionality are compromised.

Yet another potential issue with a balloon that fails to return to a low profile condition after expansion is embolization of tissue or constituent materials within the body lumens due to the balloon dragging on or across the surface of the surrounding walls. It is not uncommon for the lumens of arteries for example to have plaque and thrombus that could easily detach and embolize if manipulated too vigorously and as such this practice should be avoided if possible.

The present invention addresses these needs.

SUMMARY OF THE INVENTION

The various embodiments of the subject invention included herein provide devices, systems and methods for aiding the regrooming or refolding of balloons upon deflation. The scope of the inventions in this specification includes methods and devices that reduce the profile of balloons after deflation, reduce or eliminate wings, highpoints, irregularities, bunching, thickening, and the like, and facilitate passage of a deflated balloon through a body void or lumen, or through a medical device such as a guide catheter, guide sheath, femoral or radial introducer sheath, and the like.

The invention described in this specification comprises balloon catheter based devices and means and methods of use which enable safe and effective regrooming of the balloon. The action of regrooming may take place during the deflation of the balloon (as part of the deflation step) or as a procedural step that follows deflation of the balloon. In one embodiment of the invention, the device consists of an elongate shaft with a continuous lumen or lumens connecting the proximal and distal end, an interior and exterior. The proximal end may be connected to a hub that facilitates injection or withdrawal of fluid, air or other media. The distal end may be connected to an expandable member that has a continuous lumen or lumens connecting the proximal and distal end. The distal end of the expandable member may be connected to a tip that may consist of a cylinder with or without a lumen. The cylinder may be shaped in a coil or covered with a coil to provide flexibility and to be atraumatic. The distal tip of the device could have features to reduce trauma such as a bevel or a ball or bullet shape to reduce the chance for trauma during medical procedures.

In one embodiment, the expandable member is substantially or completely covered by an elastic or compliant sheath or jacket or cover tube. The sheath, jacket, or cover tube may be bonded to any combination or all of the following elements: the tip, the elongate member or the expandable member. Bonding may consist of chemical means or mechanical means well known in the art (including, but not limited to cyanoacrylate adhesive bonding, UV adhesive bonding, swaging, welding, crimping, screwing, heat welding, ultrasonic welding, soldering etc). The durometer of the sheath may differ from the underlying expandable member. In one embodiment, the expandable member is a balloon and the durometer of the sheath positioned over it may be greater than that of the balloon. The sheath may or may not apply an inward radial force on the balloon when it is in the unexpanded condition. The balloon may be inflated by introducing liquid, air or other media into the hub of the elongate member raising the pressure inside the balloon and eliciting a change from an unexpanded condition to an expanded condition. In the expanded condition, the balloon may display a geometric change such as a change in length, diameter, aspect ratio or the like. The sheath would conform to the balloon in both its unexpanded (or unpressurized) and expanded (or pressurized) condition. When the balloon is deflated, the sheath could exert a recoil force on the expandable member and compress the balloon to a geometry that mimics the unpressurized internal lumen of the sheath returning the system to a condition that is substantially equivalent to the starting condition (i.e. prior to the pressurization) and/or usable for subsequent treatment without removal from the patient.

In another embodiment, the elastic or compliant sheath or jacket or cover tube described above can be replaced by a rigid elongate tube or sheath that can be retracted and/or advanced to partially and/or fully uncover and/or cover the expandable member. The rigid elongate tube or sheath has a distal and proximal end, the distal end disposed in a location proximal or within the expandable member, and the proximal end disposed at the proximal section of the catheter. The distal end of the rigid elongate tube or sheath may partially cover the expandable member such that the distal section is uncovered and the proximal section is covered to allow expansion of the uncovered section to a dimension larger than the covered section. The expansion of the expandable member can be achieved using mechanical, pneumatic, or hydraulic means. The expanded distal section may be a useful method in precisely locating the opening of a luminal narrowing by retracting or pulling the expandable member after it has been expanded and has crossed the lumen narrowing. The expansion of the full expandable member length can be performed by fully retracting the moveable elongate tube or sheath, fully exposing the expandable member. After expansion, the expandable member can be collapsed (by mechanical or hydraulic/vacuum means). The moveable elongate tube or sheath may also be used to improve the collapsed dimension of the expandable member. Advancing the elongate tube or sheath distally until it covers the entire length of the expandable member performs the act of collapsing the expandable member to its original profile.

In another embodiment, the dilatation catheter consists of an elongate shaft with a continuous lumen or lumens connecting the proximal and distal end. The distal end of the elongate shaft is connected or continuous with the proximal end of the expandable member and the proximal end is connected to a proximal, slidable adapter. Within a lumen or within one of the lumens of the elongate shaft, one or more inner members (e.g. a wire and/or a tube) that has proximal and distal ends is provided, the proximal end attached to the catheter hub located proximal of the elongate shaft and the distal end attached to the distal end of the expandable member. Preferably, the elongate shaft is configured to move or slide over the inner member to allow the proximal end of the expandable member to move distally or proximally. When the expandable member is expanded to a larger dimension or diameter, its length changes to a shorter dimension relative to its collapsed or relaxed length. Since the distal end of the expandable member is attached to the distal end of the inner member that is stationary, the distal end of the expandable member remains in a stationary position (i.e. fixed at the same relative position), thus the proximal end of the expandable member moves towards the distal direction as it shortens in length. Consequently, the elongate shaft attached or continuous with the proximal end of the expandable member also moves towards the distal direction. On the other hand, when the expandable member is collapsed to its original dimension or profile (i.e. collapsed diameter), its length extends to a longer dimension or back to its original collapsed length. The stretching of the expandable member to its original collapsed length may be made possible by incorporating a biasing mechanism at the proximal end of the elongate shaft that actively applies tension force to the elongate shaft and the proximal end of the expandable member. Alternatively, the expandable shaft can be manually retracted in place of incorporating a biasing mechanism. Stretching the expandable member in the collapsed configuration allows refolding or contracting into a low diametrical, dimensional profile.

In accordance to this aspect of invention, the biasing mechanism (e.g. spring or gas or fluid pressure, etc.) is incorporated in the assembly of the slidable adapter and catheter hub. The catheter hub has a distal end, a proximal end and a port or mechanism that is used for means of expanding and contracting the expandable member. The slidable adapter attached to the proximal end of the elongate member is coupled with the distal side of the catheter hub and is free to move in the lateral or longitudinal direction. The inner member is attached to the proximal side of the catheter hub and remains stationary. The slidable adapter is proximally biased by means of a biasing mechanism that actively applies tension to the elongate shaft that is attached or is continuous with the proximal end of the expandable member. When the expandable member is expanded, the expansion causes the expandable member to shorten in length resulting in the exertion of tension force applied to the elongate shaft that is in turn transmitted to the slidable adapter attached at the end of the elongate shaft. The opposing tension force applied by the biasing mechanism is overcome by the tension force applied by the shortening of the expandable member, thus causing the elongate shaft to move distally. When the expandable member is collapsed, there is no tension force generated at the proximal end of the expandable member, thereby causing the elongate shaft to move proximally as it is pulled proximally by means of the biasing mechanism.

In all embodiments of this invention, a marker or multiple radiopaque markers may be used to help visualize the location and/or state (e.g. expanded or unexpanded, geometry etc.) of the expandable member or any component of the catheter using x-rays, fluoroscopy, ultrasound or any other visualization modality when direct visualization is not preferred, desired or possible. For example, marker bands may be placed at or under or over the proximal and/or distal edges of the expandable members. The markers could be attached using processes known in the art including but not limited to swaging, crimp, adhesive bonding or the like. Alternatively, the marker bands could be applied or painted on as a surface coating. The marker bands could be made of platinum, platinum/iridium alloys, gold, polymers with fillers including but not limited to tantalum, barium sulfate and the like, any ionic and non-ionic contrast agents etc.

As such, the key improvement of this invention is to provide a device based means to rapidly re-groom a balloon (especially large diameter balloons) after expansion helping the balloon to assume a substantially low profile to facilitate safe and easy passage through guide catheters (or equivalent accessory devices), passage into and out of tissues and lumens (especially restricted lumens) and safe retraction back into guide catheters after deployment. Another key improvement of this invention is to use this re-grooming capability to simply and ease inflation and deflation of the same balloon in the same target anatomy or at various locations in the anatomy or body peri-procedurally, and to accomplish the multiple inflations and deflations without removal of the balloon catheter from the patient. This improvement would save the physician procedure time related to removing the device from the patient for manual re-grooming, mitigate challenging catheter maneuvers required for crossing restricted tissues spaces or lumens because the profile is too high, and enable safe, rapid passage of the device to and from guide catheters (or equivalent if used in a given procedure). In the context of treatment of chronic rhinosinusitis, the regrooming balloon would provide great utility in easing atraumatic passage through inflamed mucosal tissues in the nasal cavity and paranasal sinuses. Further, the regrooming capability enabled by the embodiments of the invention would facilitate the treatment of multiple sinuses (e.g. maxillary, frontal, and/or sphenoid) on one or both sides of a patient with a single dilation balloon catheter. For example, the regroomable balloon of the invention may be incorporated into the inventions and methods described in co-pending U.S. patent applications 61/431,331 (Apparatus and Methods for Accessing and Treating a Body Cavity, Lumen, or Ostium) and 61/487,911 (Sinus Dilation Catheters with Guiding Capability for the Office Based Setting) herein incorporated in full by reference.

These and other objects, advantages, and features of the invention will become apparent to those persons skilled in the art upon reading the details of the disclosure as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIGS. 4A-4C are longitudinal cross-sectional details of the dilatation catheter that has an inner member tubing, showing the sequence of expanding and collapsing the expandable member and a wire inserted within the lumen of the inner member, in accordance with the present invention.

DETAILED DESCRIPTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Figure 1A:
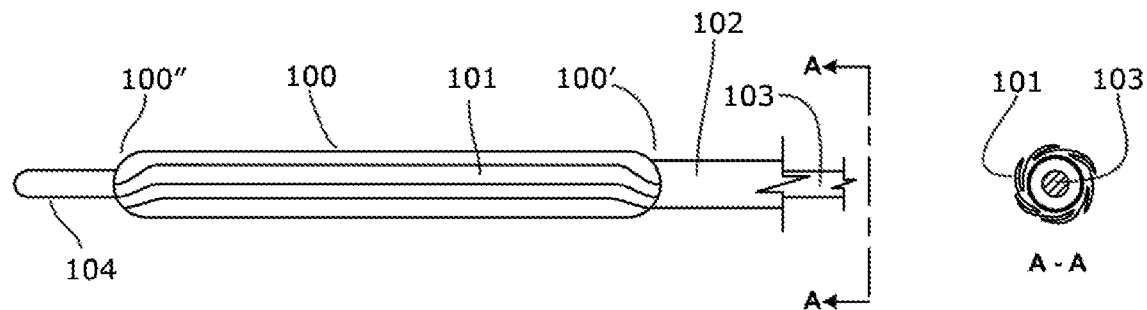
FIGS. 1A-1C depict a balloon in the folded, inflated, and deflated/winged states.
Figure 1B:
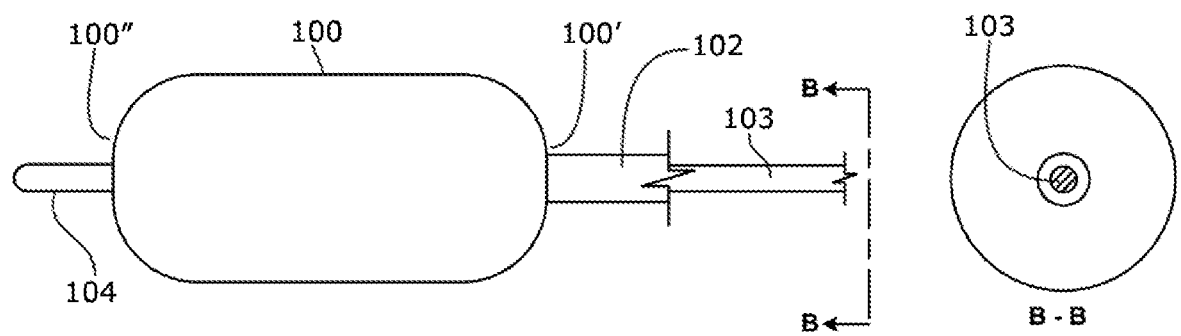
Figure 1C:
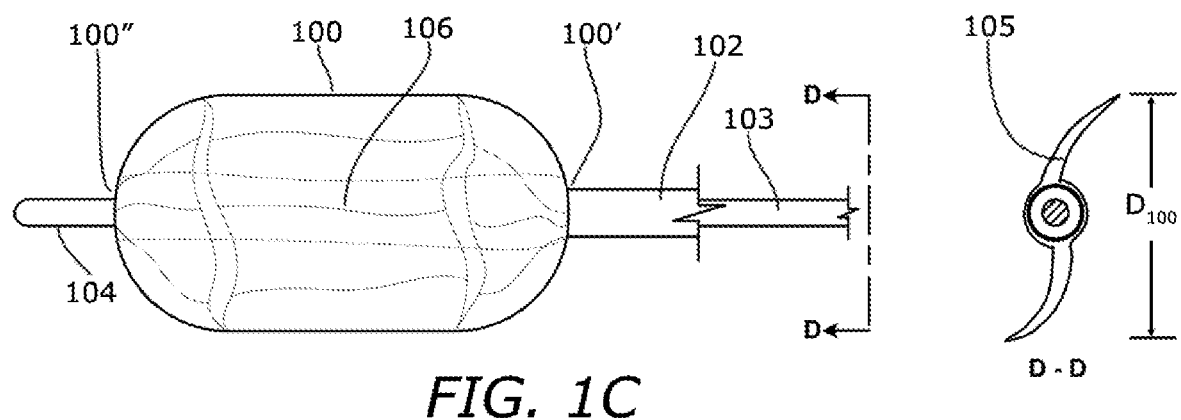

FIGS. 1A-1C depict the process of inflating and deflating a commonly used balloon dilatation catheter, further showing the distal segment of the said balloon dilatation catheter and how the balloon 100 may refold with winging when deflated after the initial inflation of the multi-pleat (i.e. more than 2 pleats), folded balloon. FIG. 1A illustrates the initial configuration of a multi-pleat, folded balloon 100, showing a proximal end 100' at a given distance away from the distal end 100". Conventional processing methods including pleating, folding, wrapping, stretching and the like to produce low dimensional profiles prior to initial inflation. The balloon 100 may be gathered in multi-pleat folds 101 and wrapped around the inner member 103 in one direction (best shown in FIG. 1A: cross-section view A-A) thereby reducing the initial collapsed diameter (or crossing profile). The distal end of the balloon 100" is attached (e.g. bonded, ultrasonic welded, crimped, heat fused, and other processes well known to the art) to an atraumatic tip 104 and the proximal end of the balloon 100' is attached (e.g. bonded, ultrasonic welded, crimped, heat fused and other processes well known to the art) to the catheter shaft 102. FIG. 1B illustrates the inflated configuration of the balloon 100 after the catheter has been pressurized through the introduction of inflation media such as air, water, saline, contrast, mixture of saline and contrast, or other gas or fluid media. In the case of a pre-stretched folded balloon as shown in FIG. 1A, the distance between the proximal end 100' and distal end 100" of the balloon 100 may typically decrease as the balloon assumes its fully inflated or expanded geometry. Expansion and full inflation at high pressures may also eliminate or iron out the multi-pleat folds 101 as shown in FIG. 1B. FIG. 1C illustrates the natural collapsed configuration of the balloon 100 from a commonly used balloon dilatation catheter after it has been fully deflated. This collapsed configuration may typically result in the formation of uncontrolled wrinkles 106 and a dual-pleat fold (or wings) 105; thereby increasing the overall collapsed crossing profile of the balloon 100 beyond that of its initial, unexpanded state shown in FIG. 1A. This may render it difficult for the device to navigate and for the balloon 100 to cross or re-cross narrowed body lumens or openings upon re-use of the same device or to be safely and quickly removed through the lumens of typically used accessories (e.g. guide catheters). Further, a user may need to remove the device from the patient to manually re-groom the balloon in order to force the balloon to fold back in a smaller profile.

Figure 2A:
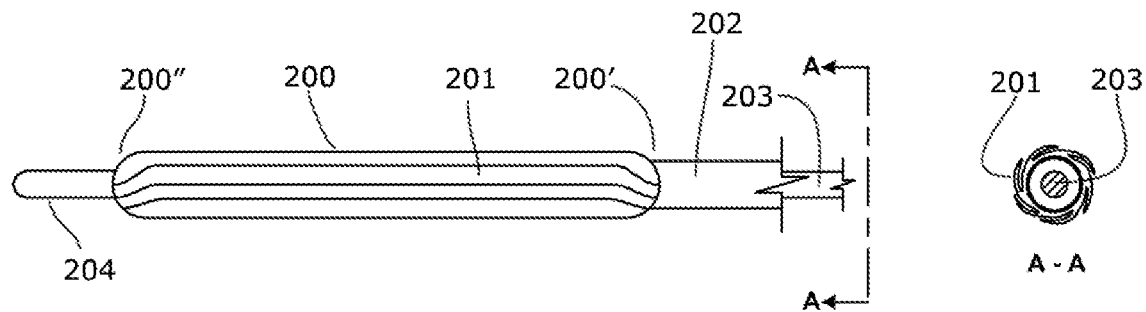
FIGS. 2A-2C depict a balloon in the folded, inflated, and deflated/regroomed states.
Figure 2B:
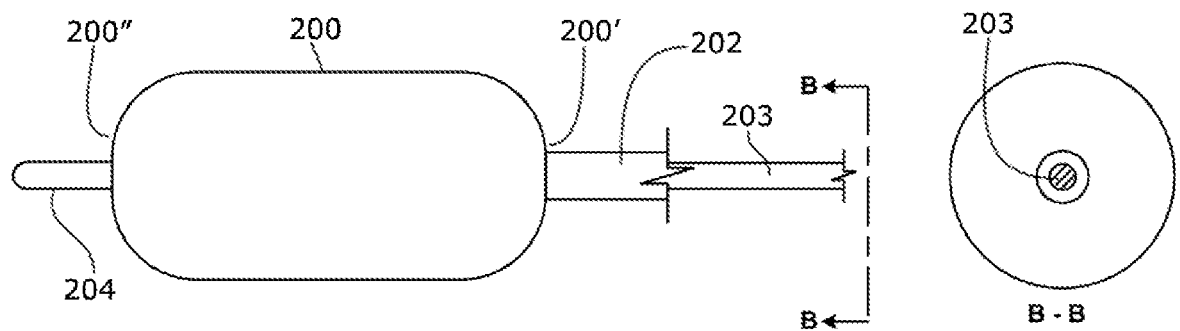
Figure 2C:
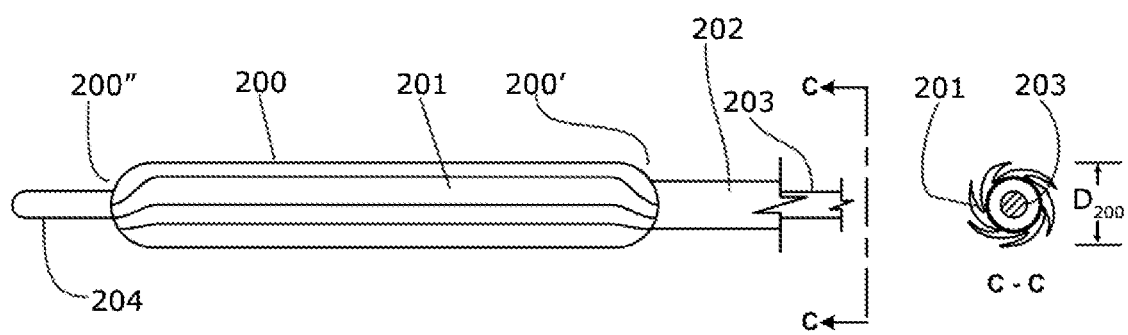

FIGS. 2A-2C depict a system similar to that shown in FIGS. 1A-1C, in which a balloon 200 is bonded to the elongate, catheter shaft 202 on the proximal end and to a fixed inner member 203 on the distal end with an atraumatic tip 204 attached to the distal most end of the system. Balloon 200 has multiple pleats 201 in the pre-inflated state as shown in FIG. 2A. However, this system employs a mechanism that applies an active tensile load on the proximal end 200' of the balloon 200. FIG. 2B illustrates the balloon 200 in its inflated state, showing a reduced distance between the proximal end 200' and distal end 200" of the balloon 200. FIG. 2C depicts an embodiment of the invention wherein a tensile load is applied to the proximal end 200' of the balloon 200 with the distal end 200" held fixed via its bond (not shown) to inner member 203. This results in the balloon having assuming approximately the same distance between proximal end 200' and distal end 200" as seen in its initial pre-inflated configuration shown in FIG. 2A. A comparison of FIGS. 1C and 2C illustrates the effect of retracting the proximal end 200' of the balloon 200 away from the distal end 200" during deflation; the collapsed balloon 200 has refolded into a multi-pleat (i.e. more than two pleats) configuration 201, thus the collapsed crossing profile of the balloon 200 (FIG. 2C: $D_{200}$) is reduced in comparison to that of balloon 100 (FIG. 1C: $D_{100}$). The subsequent figures illustrate several embodiments of the invention that provide designs and methods for re-grooming or re-folding a balloon or similar expandable member back to a substantially collapsed dimensional profile without the need to manually manipulate, massage or compress said balloon or similar expandable member.

Figure 3A:
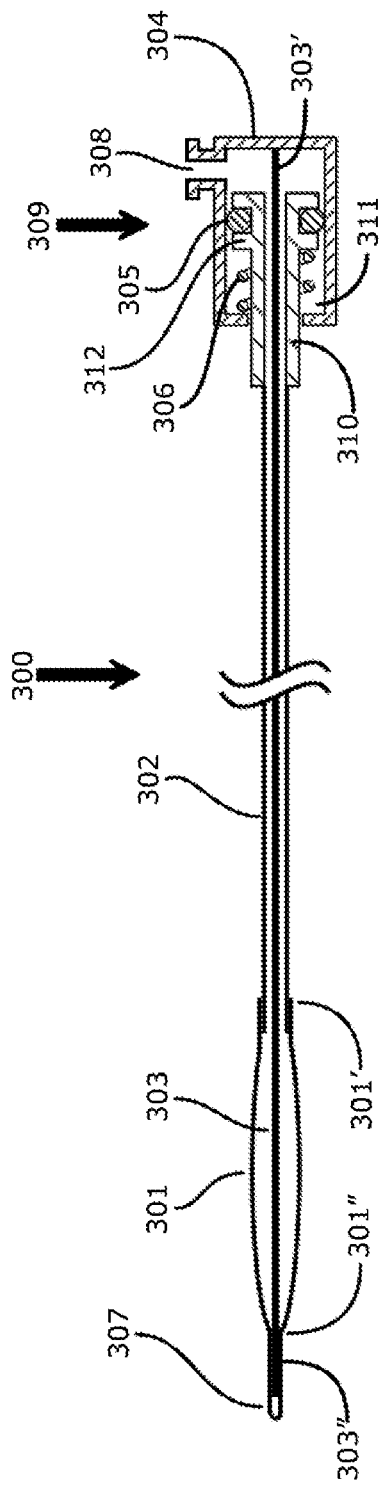
FIGS. 3A and 3B are longitudinal cross-sectional details of the dilatation catheter that has a fixed wire inner member, with the expandable member shown in the collapsed and expanded configuration, respectively, in accordance with the present invention.
Figure 3B:
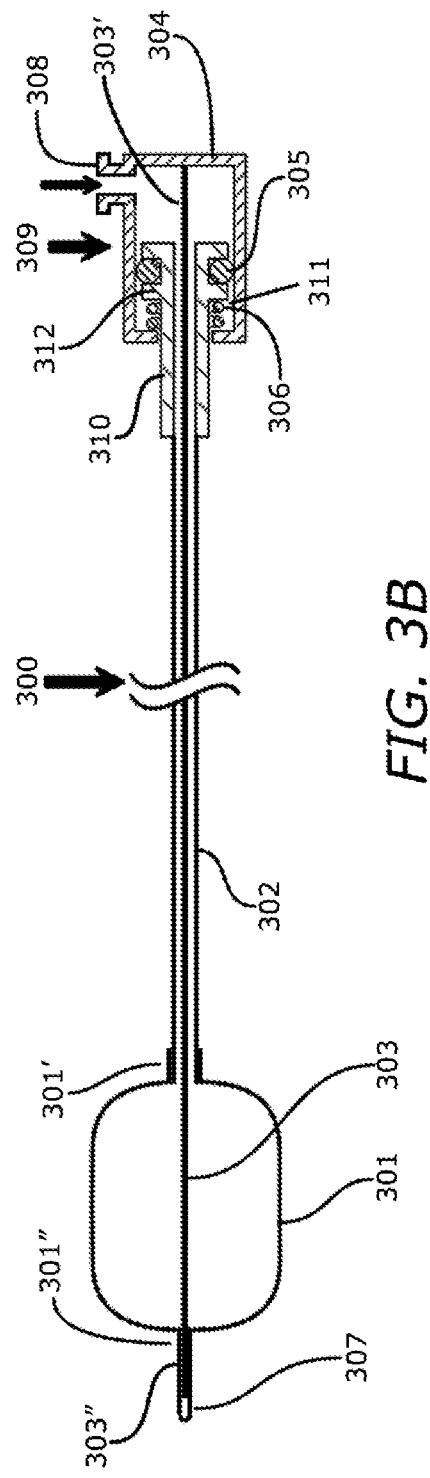

FIGS. 3A and 3B show a preferred embodiment of an apparatus 300 used for dilatation of a narrowed lumen or opening of a human or animal and a method for providing a means to re-groom or refold the balloon for subsequent or multiple uses. The apparatus 300 is a dilatation catheter with an expandable member 301 having proximal end 301' and distal end 301" and a fixed inner member 303 that has a biasing mechanism 311 designed to collapse the expandable member 301 into a low crossing profile after it has been expanded or inflated one or more times. Generally, the apparatus 300 is comprised of a distal atraumatic tip 307, an expandable member 301, an elongate, catheter shaft 302, an inner member 303, a catheter hub 304, gasket 305, and a spring 306. The atraumatic tip 307 is attached to the distal end 301" of the expandable member 301 and inner member 303. The atraumatic tip 307 may be made of flexible, soft, elastic and/or compliant materials known in the art including, but not limited to low durometer plastics or polymers (e.g. PEBAX® 53D, Silicone rubber, Low density PE, urethanes and the like) or a metallic or nonmetallic coil wound and attached over the distal end of the inner member 303 using any of the processes known in the art including, but not limited to adhesive bonding, welding, thermal bonding, ultrasonic welding, swaging, crimping, and the like. The distal end 301" of expandable member 301 is attached to the distal end 303" of the inner member 303 and made preferably of a semi-compliant or non-compliant balloon materials that may be activated by hydraulic means using fluid inflation media (e.g. saline, air, saline/contrast and the like). The expandable member 301 may be made from materials well known in the art including, but not limited to: nylon, PEBAX®, polyester, PET, TEFLON®, and the like.

Alternatively, the expandable member 301 may be made of substantially rigid materials in the form of a metallic braid, coil, umbrella, or a plurality of a longitudinal flat wires or the like, that may be mechanically activated or expanded and contracted by means of a linkage (not shown) disposed within the elongate, catheter shaft 302. The linkage could have distal and proximal ends, the distal end connected to the expandable member 301 and the proximal end disposed in the catheter hub 304 where a mechanism may be attached that allows expanding and contracting of the expandable member 301.

In one embodiment, the expandable member 301 may be made into an assembly using the combination of a balloon and a substantially rigid material that can be activated by mechanical and/or hydraulic means. In another embodiment, where an ultra high dilatation pressure is demanded by the desired application or desired need and where the previously mentioned materials are not capable of reaching such pressures, the expandable member 301 may be constructed from composite materials such as compounded or coextruded polymer materials and/or braided or fiber reinforced polymer or compounded polymer materials. The geometry of expandable member 301 could vary based on the processing methods used for fabrication or based on the need or the desired use or application, but generally the preferred balloon shape is a tubular cylinder with conical tapers at the distal end 301" and proximal end 301'. The expandable member 301 may be continuous with the elongate, catheter shaft 302 or it may be a separate component that may be connected or attached to the catheter shaft 302 using any of the processes known in the art including, but not limited to adhesive bonding, welding, thermal bonding, ultrasonic welding, swaging, crimping, and the like. The elongate, catheter shaft 302 is an elongate member with proximal and distal ends and may consist of a single continuous lumen or multiple lumens therethrough. The elongate, catheter shaft 302 may be constructed from materials well known in the art including, but not limited to nylon, polyimide, PEBAX®, TEFLON®, polyester, peek, urethane, composite polymers (e.g. blended or co-extruded or layered polymer materials), reinforced polymers (e.g. metal or fiber braid or coil reinforced tubing), metals (e.g. stainless steel, nickel titanium, etc) and the like. The elongate, catheter shaft 302 may have a singular stiffness or may have multiple stiffness properties along its length. The elongate catheter shaft 302 may have internal ribbings or bumps or other shapes/features (not shown) that constrain the inner member 303 within the lumen of the elongate catheter shaft 302 to prevent or minimize the said inner member 303 from assuming a wavy condition or buckling within the lumen of elongate catheter shaft 302 when the expandable member 301 is de-pressurized or deflated and assumes a stretched configuration. Disposed within a lumen of the elongate, catheter shaft 302 is an inner member 303, that may be constructed from well known materials and constructions including, but not limited to a solid metallic core wire (e.g. made from stainless steel, nickel titanium, and the like), or a composite inner member assembly (e.g. coil or braid over a core wire, polymer coated core wire, etc) which has distal and proximal ends, the distal end 303" attached to the distal end 301" of expandable member 301 and the proximal end 303' attached to the proximal end of the catheter hub 304. The inner member 303 may have external ribbings or bumps or other shapes/features (not shown) that constrain the inner member 303 within the lumen of the elongate shaft 302 to prevent the said inner member 303 from assuming a wavy condition or buckling within the lumen of elongate shaft 302 when the expandable member 301 is de-pressurized or deflated and assumes a stretched configuration. Generally, the catheter hub sub-assembly 309 includes a catheter hub 304 coupled with the slidable adapter 310 to which the proximal end of the elongate, catheter shaft 302 is attached. The catheter hub 304 has proximal and distal ends; the inner member proximal end 303' is bonded to the catheter hub 304 proximal end and the slidable adapter 310 is mounted to the distal end of the catheter hub 304. The catheter hub 304 has an access port 308 where an accessory (e.g. inflation device, not shown) is attached as a means to expand and contract the expandable member 301. In the embodiments of FIGS. 3A and 3B, the biasing mechanism 311 consists of a spring 306 positioned within the catheter hub 304, and mounted over the slidable adapter 310 in between the distal end of the catheter hub 304 and the gasket flange 312 located behind the slidable adapter 310. The spring may be made of materials known in the art including, but not limited to metallic (e.g. stainless steel, nickel titanium, etc), or non-metallic materials (e.g. nylon, TEFLON®, fiber, etc), or composite materials (i.e. made by combining metallic and non metallic materials). The spring constant may be chosen to exert a sufficient biasing force so that the expandable member assumes a stretched configuration when it is in the collapsed, deflated or contracted state. In the biasing mechanism 311 shown in FIGS. 3A and 3B, the spring 306 may be free floating over the slidable adapter, however its distal and proximal ends may be affixed to the distal end of the catheter hub 304 and the gasket flange 312, respectively. The mounted spring 306 has a length that may be fully extended or partially compressed such that the slidable adapter 310 is actively biased in the proximal direction and pushed away from the distal end of the catheter hub 304. The force applied by the spring 306 resting against the gasket flange 312 of the slidable adapter 310 results in a tensile force transmitted to the elongate catheter shaft 302 attached to the proximal end of the expandable member 301. The tensile force applied by the catheter shaft 302 in turn pulls the proximal end 301' of the expandable element 301 to stretch or expand and pull away from the distal end 301" towards the proximal direction. Alternatively, the spring 306 can be placed behind and in between the slidable adapter 310 and the catheter hub 304 proximal end, where one end of the spring 306 may be affixed to the slidable adapter 310 and the other end affixed to the proximal end of the catheter hub 304. In this configuration, the mounted spring 306 has a length that may be fully extended or partially extended or tensioned such that the slidable adapter 310 is actively biased in the proximal direction and pulled away relative to the distal end of the catheter hub 304.

Referring to FIG. 3B, the expandable member 301, preferably a balloon, may be activated or inflated by means of introducing a hydraulic (i.e. air or fluid) pressure to the access port 308 using an inflation/deflation device known in the art (e.g. indeflator, syringe) and may be deflated using the same or separate inflation/deflation device. Alternatively, the expandable member 301 may be constructed to be expanded and contracted using mechanical means, as previously described. The gasket 305 mounted over the slidable adapter 310 provides a fluid or airtight seal between the catheter hub 304 and slidable adapter 310 and is free to move or slide within the inner surface of the catheter hub 304. The gasket 305 may be made of polymer materials know in the art including, but not limited to silicone, santoprene, neoprene, and other elastomeric and thermoplastic rubber materials.

Further referring to FIG. 3B, a method is provided to expand and contract the expandable member 301 into a low profile when it is deflated following the first inflation. When inflation media is introduced through the access port 308 of the catheter hub 304, the inflation media is transmitted to the balloon expandable member 301 through the lumen of the elongate catheter shaft 302 that provides communication between the expandable member 301 and catheter hub 304. The pressure generated by the inflation device exerts internal pressure to the inside wall of the balloon expandable member 301 and causes it to expand in size until a full inflation diameter is reached. Simultaneous to the inflation of the balloon expandable member 301, the distal end 301" and proximal end 301' of the expandable member 301 move closer relative to each other, causing the overall balloon length to decrease. The distal end 301" of the expandable member 301 is attached and fixed to the distal end 303" of the inner member 303, and the proximal end 301' of the balloon expandable member 301 is floating and free to move, thus the proximal end 301' is pulled distally as the balloon expandable member 301 is inflated. The shortening of the expandable member 301 generates tensile force in the distal direction, pulling the elongate catheter shaft 302 distally as the balloon's proximal end 301' moves distally. The elongate catheter shaft 302 attached to the slidable adapter 310 moves distally in unison. The applied tensile force transmitted to the elongate catheter shaft 302 and the slidable adapter 310 overcomes the active opposing force exerted by the spring 306 causing the spring to compress and shorten in length as shown in FIG. 3B. When the inflation pressure in the balloon expandable member 301 is released and a vacuum pressure is applied to contract or deflate the expandable member 301, the spring 306 expands in length and pulls the elongate catheter shaft 302 proximally with respect to catheter hub 304. The proximal motion of the elongate catheter shaft 302 in turn pulls the proximal end 301' of expandable member 301 away from the distal end 301" causing the balloon expandable member 301 to spread or stretch in length. The active pulling of the balloon expandable member 301 proximal end 301' initiates the balloon to form multiple wings or pleats, uniformly re-grooming the expandable member 301 into a relatively low dimension, contracted or deflated crossing profile.

FIGS. 4A through 4C illustrate yet another embodiment showing the apparatus 400 for dilating a narrowed lumen or opening of a patient and a method for providing a means to re-groom or refold the balloon for subsequent use featuring the addition of a through lumen that can accept passage of guidewires and similar apparati. These figures also depict the sequence by which the balloon expandable member 401 is inflated from a collapsed state, then deflated or contracted back to the collapsed state. FIG. 4A is a representation of the apparatus 400, similar to apparatus 300 shown in FIGS. 3A and 3B, where the expandable member 401 is shown in the collapsed and extended configuration and where the biasing mechanism 411 is shown to bias the slidable adapter 410 in the proximal position. FIG. 4B shows the expandable member 401 in the expanded or inflated configuration where the proximal end of expandable member 401 taper has pulled or moved distally after introducing an inflation media through the access port 408 and where the slidable adapter 410 has been pulled to a distal position. Finally, FIG. 4C is a representation of an expandable member 401 shown in the collapsed and extended configuration after deflating or contracting the expandable member 401 and where the biasing mechanism 411 is shown to bias the slidable adapter 410 in the proximal position. Apparatus 400 is generally identical in construction, processing assembly and operating principle as apparatus 300 shown in FIGS. 3A and 3B, the difference being the fixed inner member 303 is replaced by a fixed inner member 403. The fixed inner member 403 is an elongate tube that has distal and proximal ends and may consist of a single lumen 412 that is, or multiple lumens that are, continuous from the proximal to distal ends. The inner member lumen 412 may be used to receive a guidewire 413, as shown in FIG. 4C, or other similar devices needed to navigate and/or direct the apparatus 400 to the desired target site. An additional lumen or lumens may be provided to the inner member 403 and may be sized to receive other equipment such as diagnostic or therapeutic devices (e.g. light wires, endoscopic wires, ultrasound wires, flow sensor wires or other diagnostic or therapeutic devices) needed for the desired application. One of the additional lumens may also be used to receive medications or other fluid media needed to be delivered at target treatment sites or alternatively to aspirate fluids out of the body. The inner member 403 may be made of a singular material or a composite (i.e. more than one) material (e.g. coil or braid reinforced tube, coextruded tube with multiple layers, etc) and may be constructed to have one stiffness along the entire length or multiple stiffness in various sections along the entire length.

Figure 5A:
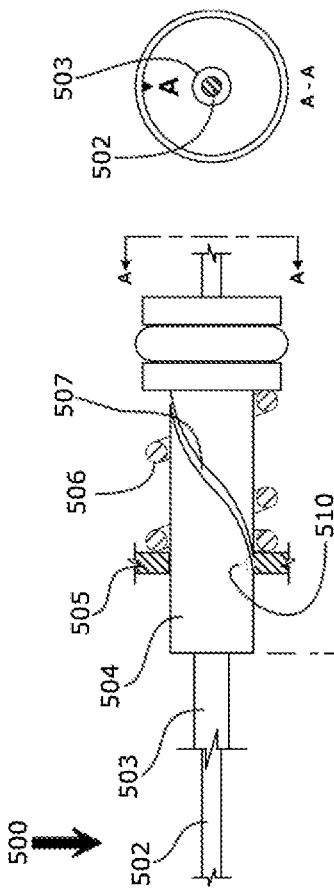
FIGS. 5A-5C are longitudinal and radial views of a balloon catheter that has a movable shaft, showing the sequence of expanding and collapsing the balloon in accordance with the present invention.
Figure 5B:
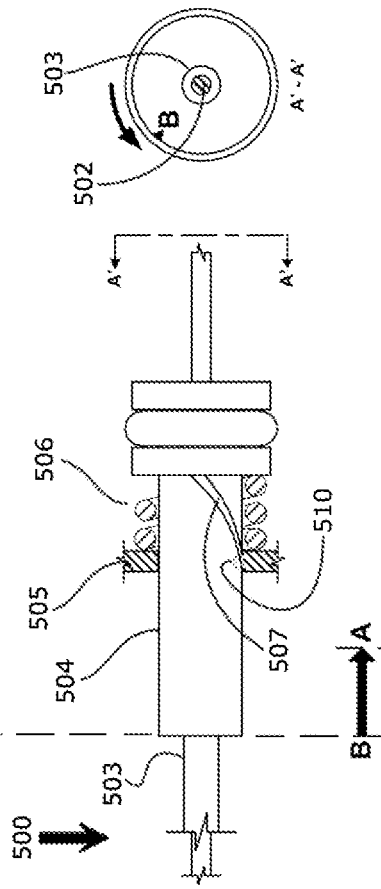
Figure 5C:
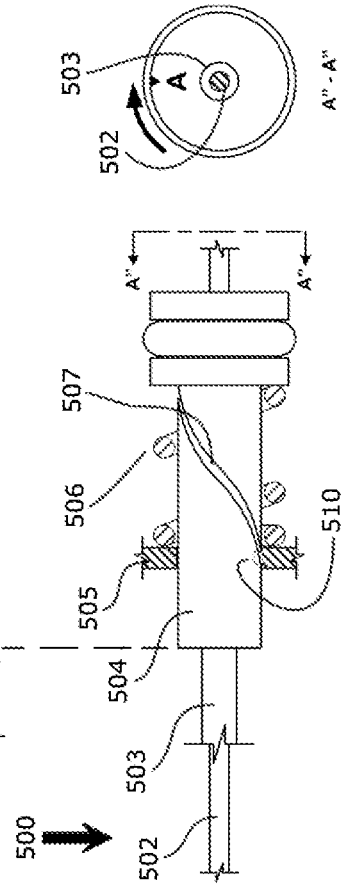

FIGS. 5A-5C depict another embodiment of the catheter 500 of the invention, in which the expandable member is rotated about the fixed inner member 502 as it collapses, by incorporating a biasing mechanism similar to that of biasing mechanism 311 previously described with the addition of a rotational feature to the mechanism. The slidable adapter 504 may incorporate a spiral rail feature 507 (e.g. spiral groove, cam surface or track, etc.) such that when coupled with the catheter hub 505 (partial section shown), through a linkage pin 510 the movement of slidable adapter 504 from distal to proximal direction causes slidable adapter 504 to turn or rotate relative to the longitudinal central axis of the catheter. The sequence of twisting and untwisting during inflation or pressurization and deflation or depressurization of the expandable member 501 is illustrated in the cross sections A-A, A'-A' and A"-A" of FIGS. 5A-5C. Position A in Cross section A-A of FIG. 5A shows the initial (12 o clock) position of the slidable adapter prior to inflation or pressurization of the balloon expandable member 501. In general, when the balloon is in the collapsed state (for example) as shown in FIG. 5A and FIG. 5C, the biasing mechanism spring 506 may be fully extended or partially compressed such that the slidable adapter 504 is actively biased in the proximal direction and pushed away from the distal end of the catheter hub 505 at or below atmospheric pressure. Position B in Cross section A'-A' of FIG. 5B shows the counter-clockwise rotation of the slidable adapter 504 to an approximately 10 o clock position showing a compression of the biasing mechanism spring 506 to accommodate the shortening of the balloon expandable member 501 as it undergoes inflation or pressurization. Finally, upon depressurization or deflation of the balloon expandable member 501, the slidable adapter 504 rotates clockwise and returns to its initial 12 o clock position (i.e. position A in cross section A"-A") and the biasing mechanism spring 506 contributes a spring force to help return the slidable adaptor 504 to the initial position shown in FIG. 5C as it undergoes deflation or de-pressurization. It is also illustrated in FIGS. 5A-5C that the slidable adapter 504 moves distally in the longitudinal direction during inflation or pressurization of the expandable member 501 from the A to the B position in FIG. 5B. Finally, as the balloon expandable member 501 returns to its initial position upon depressurization or deflation the slidable adaptor 504 is shown to move from position B to A. The rotational motion of slidable adaptor 504 is transmitted to the elongate catheter shaft 503. The rotational motion of the elongate shaft 503 is then transmitted to the proximal end 501' of the collapsed expandable member 501 which causes the expandable member 501 to twist in the direction of the rotation while the distal end 501" of the expandable member 501 is held fixed by the distal end of the inner member 502. It can be appreciated that the stretching and/or twisting of the collapsed expandable member 501 (i.e. stretching and/or twisting of collapsed balloon wings) may result in a lower collapsed crossing profile compared to a collapsed expandable member such as a balloon that has not been stretched and/or twisted. Additionally, the twisting and/or stretching of the expandable member 501 occur simultaneously at the moment when it is being contracted (i.e. deflated). The stretching may also result in a collapsed expandable member 501 such as a balloon that has more than two longitudinal pleats or folds. Alternatively, the stretching and/or twisting of the expandable member 501 may be performed manually by rotating the slidable adapter 504. Additionally, the catheter 500 may include a means to retain the spiral or twisted multi-pleat folds of the balloon expandable member 501 by preventing the elongate catheter shaft 503 from rotating in the direction opposite to the balloon's spiral or twist. By way of an example, the slidable adaptor 504 could feature a longitudinal rail feature (not shown) which would limit rotational motion of the slidable adaptor 504 and the elongate catheter shaft 503 by interacting with a pin (not shown) fixed in or to the catheter hub 505 allowing the slidable adaptor 504 to move only proximally or distally in the longitudinal direction. It would be obvious to one of ordinary skill in the art that there are numerous other ways and means of preventing rotation of the slidable adapter 504 and elongate catheter shaft 503 and this example is not limiting.

Another embodiment for providing a means to re-groom or too help the balloon expandable member 501 achieve a low profile to facilitate subsequent or multiple uses in the same procedural setting includes inducing a twist to the multi-pleat folds 101 (FIG. 1A) in the expandable member 501 prior to, or during the process of, or after coupling the slidable adapter 504 to the catheter hub 505 (partially shown in FIGS. 5A to 5C). This may be accomplished by several means which may be applied to any of the catheter design platforms described in FIGS. 3A to 3B and 4A to 4C or to any other catheter design platform such as a rapid exchange or mono-rail catheter (not shown), etc. For example, the multi-pleat folds 101 (FIG. 1A) of the balloon expandable member 501 may be formed into a twisted configuration as shown in FIG. 5A by means of a balloon folding and/or wrapping process prior to assembling the elongate catheter shaft 503 to the slidable adapter 504 and/or catheter hub 505 or to other components of the catheter 500 where the proximal end of the catheter shaft 503 is being attached. For example, in a rapid exchange or mono-rail catheter configuration (not shown), the distal end of the elongate catheter shaft 503 may be attached proximal to the expandable member 501 and the proximal end of the elongate catheter shaft 503 would be attached near or adjacent to the guide wire exit port (not shown). Alternatively, in addition to the already twisted balloon multi-pleat folds 101 (FIG. 1A), the catheter shaft 503 may also be rotated about the fixed inner member 502 in the same direction as the folded balloon twist. This would be done prior to assembling the elongate catheter shaft 503 to the slidable adapter 504 and/or catheter hub 505 or to other components of the catheter 500 where the proximal end of the catheter shaft 503 is being attached. The twisting may also be introduced by means of configuring the balloon expandable member 501 to include multi-pleat folds oriented along the longitudinal axis of the catheter shaft 503 and then rotating the said elongate catheter shaft member 503 either clockwise or counterclockwise about the fixed inner member 502. This could be accomplished (for example) during the process of assembling the elongate catheter shaft 503 to the slidable adapter 504 and/or catheter hub 505 or to other components of the catheter 500 where the proximal end of the catheter shaft 503 is being attached. In this embodiment of the invention, the slidable adapter 504 may employ a spiral rail feature 507, or a cam, or a groove, or a straight rail feature (not shown), or a combination thereof, the rail feature having engaged to the linkage pin 510 coupled with the catheter hub 505. Alternatively, the slidable adapter 504 may not employ a rail feature (not shown). It would be obvious to one of ordinary skill in the art that other means of preserving the multiple pleat configuration and the spiral or twisted pattern of the multi-pleat folded balloon 501 may be employed in the construction of balloon catheter 500, with the intent of maintaining said multi-pleat folded, spiral and/or twisted configuration enabling to help the balloon expandable member 501 achieve a low profile or to re-groom or to achieve a substantially collapsed state upon de-pressurization or deflation facilitating subsequent or multiple uses in the same procedural setting.

Figure 6A:
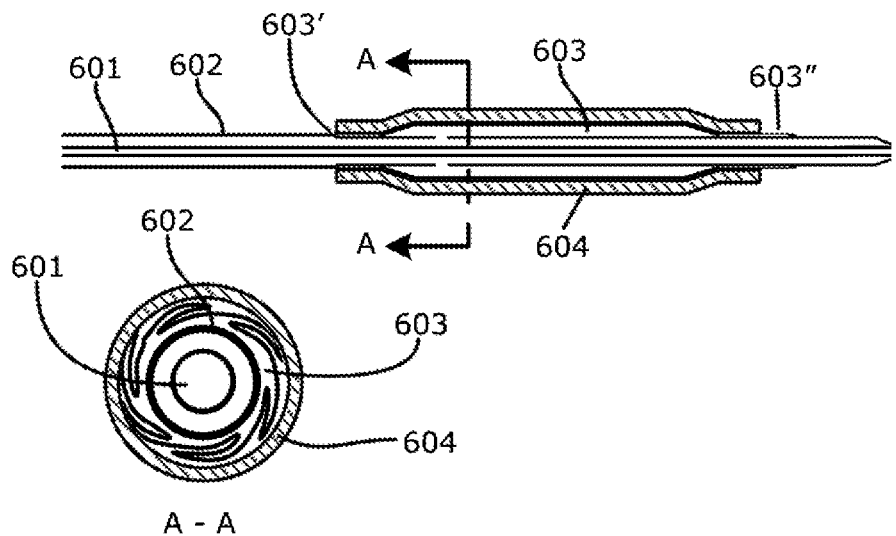
FIGS. 6A-6B are longitudinal and radial views of a balloon catheter that has a movable, rotating shaft, showing the sequence of expanding and collapsing the balloon in accordance with the present invention.
Figure 6B:
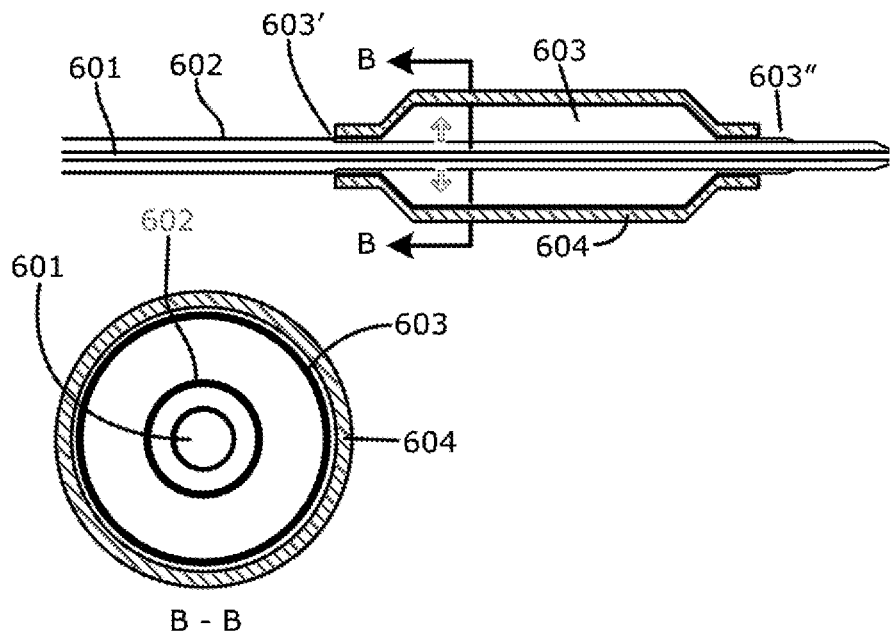

Another device and method embodiment for providing a means to re-groom the balloon for subsequent or multiple use is the employment of a coaxial sheath covering over the balloon and is shown in FIGS. 6A and 6B. FIG. 6A provides a plan view and cross section of the embodiment showing a balloon expandable component 603, a core or guidewire lumen 601, an elongate catheter shaft 602 and a sheath covering 604. The sheath 604 could be constructed of elastic or flexible materials including, but not limited to silicone rubber, latex, polyurethanes, PEBAX®, nylon, c-flex, or any thermoplastic or thermoset elastomer. The sheath 604 could be positioned to generally to partially or completely cover the expandable balloon component's 603 length thereby helping re-groom and reduce the balloon's profile. In FIG. 6A, the sheath 604 is shown completely covering the balloon expandable component while it is fully deflated. In both FIGS. 6A and 6B, the sheath member 604 is bonded to the proximal, elongate catheter shaft 602 of the device. Alternatively, the sheath 604 could be free-floating (held only by friction between the sheath 604 and the underlying balloon component 603 and/or elongate catheter shaft 602) if desired. For increased safety, it may be preferable to physically attach the sheath member 604 to the balloon component 603 at the proximal 603' and/or distal 603" ends of the balloon component 603 or to the proximal elongate shaft 602 and/or any distal tips that may be attached using a variety of means including, but not limited to heat bonding or fusing, adhesive bonding, welding, swaging or the like. It is understood that the sheath 604 may be attached to the elongate catheter shaft and/or the balloon and/or any tip at any point on these respective parts as dictated by the device design requirements. FIG. 6B goes further to depict the appearance of the balloon expandable component 603 and its sheath covering 604 when the balloon is expanded or fully inflated. The sheath 604 is shown to radially and elastically expand as the balloon grows and ultimately irons out the pleats and folds that are noted in cross section A-A of FIG. 6A. Upon deflation, elastic recoil of the sheath 604 along with the vacuum pressure applied to the balloon would return the balloon to its substantially low profile condition noted to closely mimic the original profile of the balloon prior to the first inflation depicted in FIG. 6A.

Another embodiment of the invention is depicted in FIGS. 7A-7D, wherein the apparatus 700 is configured such that the sheath 703 is a substantially rigid member that is arranged slidably and coaxially over a balloon system consisting of a elongate catheter shaft 701, an expandable balloon component 704, catheter hub 706, and a core or guidewire lumen 705. The sheath 703 is connected to a hub 702 that can be used to advance or retract the sheath with respect to the expandable balloon component 704. The substantially rigid sheath 703 would consist of an elongate member with proximal and distal ends. The sheath of this embodiment could be made from the following non-limiting list of materials: PEBAX®, nylon, urethane, silicone rubber, latex, polyester, TEFLON®, DELRIN®, PEEK, stainless steel, nitinol, platinum etc.

Figure 7A:
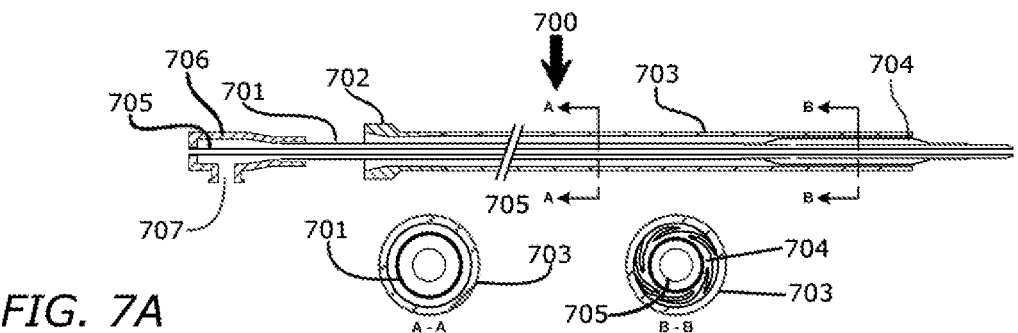
FIGS. 7A-7D depict cross-sectional views of an embodiment of a grooming sleeve for use with balloon catheters in the deflated and expanded states.
Figure 7B:
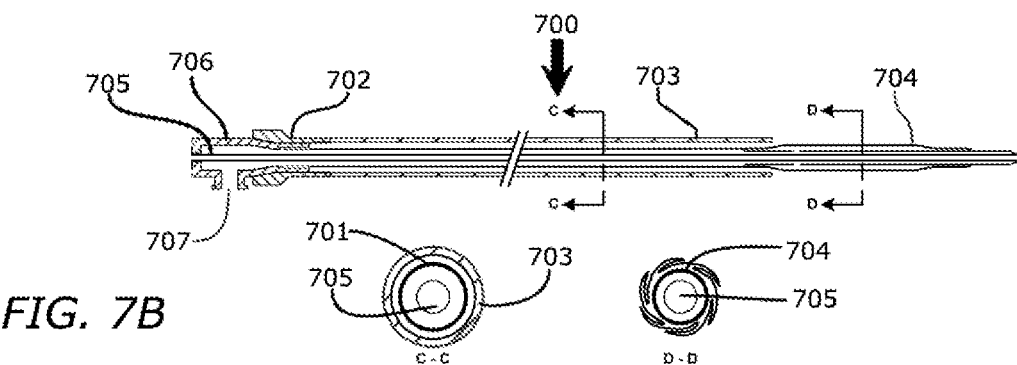
Figure 7C:
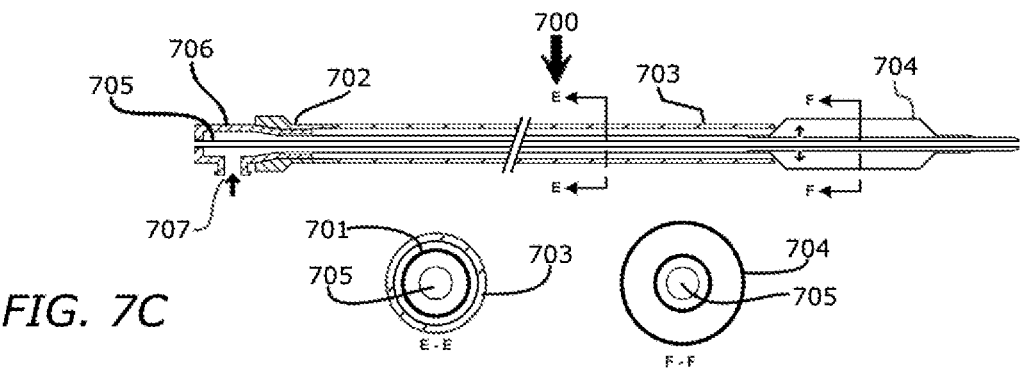
Figure 7D:
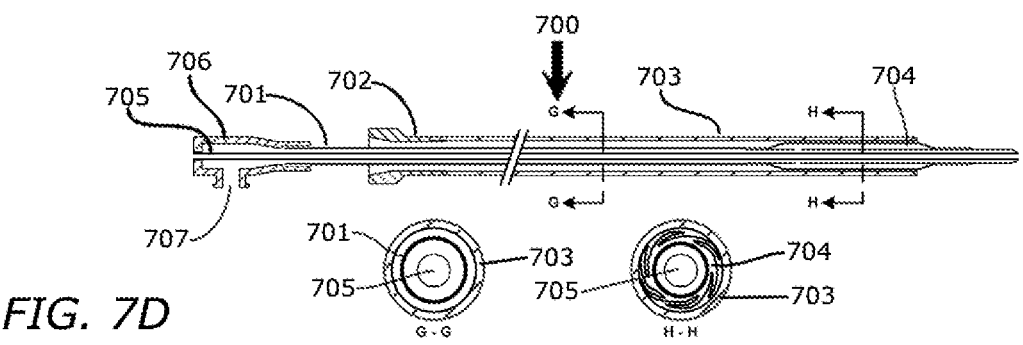
Figure 8A:
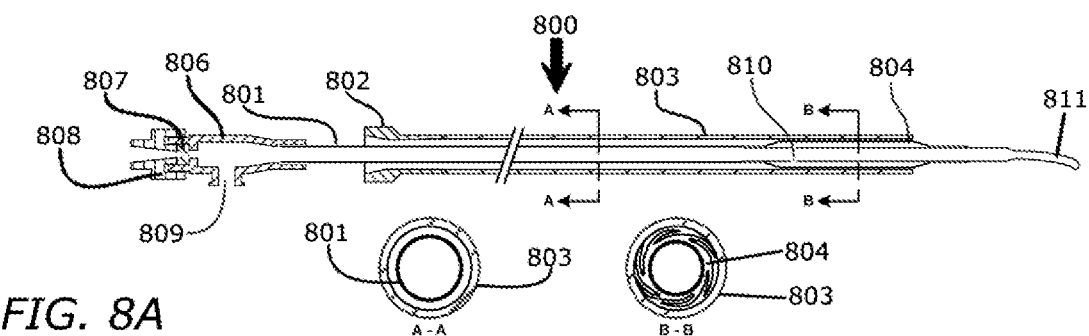
FIGS. 8A-8D depict an embodiment of a re-grooming balloon catheter with a slidably disposed capture sheath showing the sequence of expanding and collapsing the balloon in accordance with the present invention.
Figure 8B:
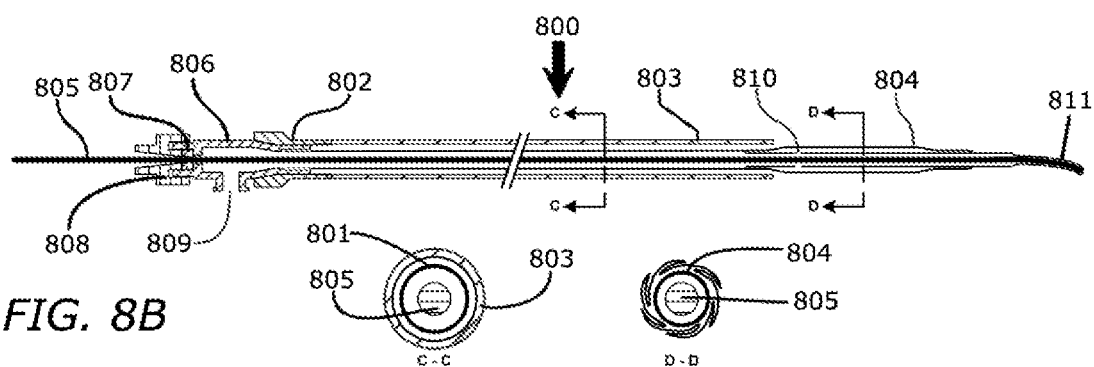
Figure 8C:
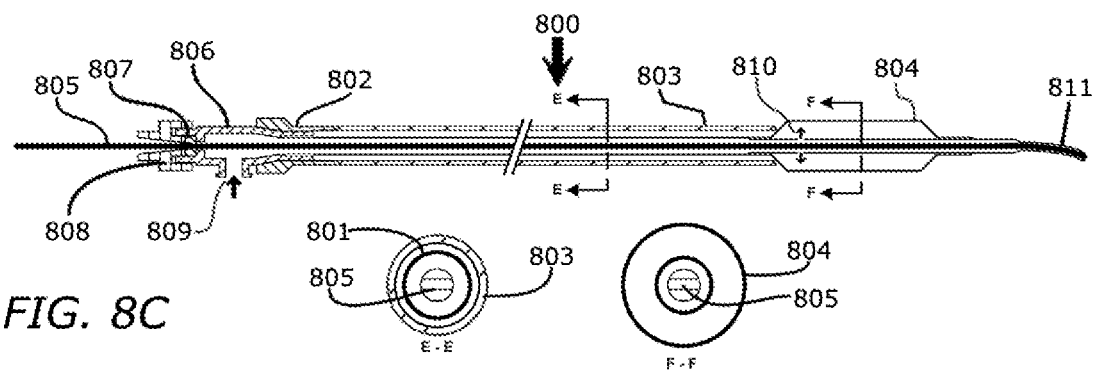
Figure 8D:
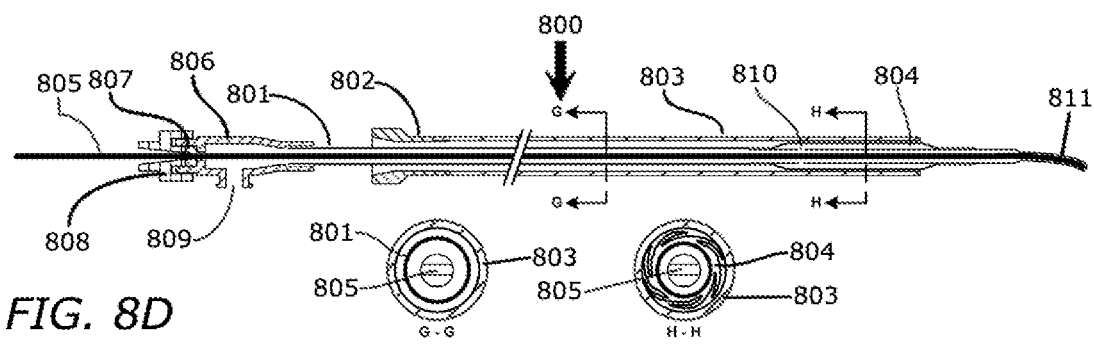

FIG. 7A provides a plan view and cross sectional views of the embodiment of the invention where the sheath 703 of the invention is positioned to completely cover the expandable balloon component 704. FIG. 7B provides a plan view and cross sectional views where the sheath 703 has been retracted proximally along the longitudinal axis of the apparatus until sheath hub 702 abuts the catheter hub 706. As seen in the cross section D-D of FIG. 7B, the balloon expandable component is now fully exposed and can be inflated and expanded as required. FIG. 7C shows the balloon catheter after inflation using a standard inflation device or equivalent (not shown) through the inflation port 707 depicting expansion of the balloon expandable component 704. The folds and pleats of the balloon expandable component 704 are noted to be ironed out (or absent) in the expanded or pressurized condition as shown in cross section F-F of FIG. 7C. Finally, FIG. 7D depicts the resheathing of the fully deflated balloon expandable component 704 using the sheath 703. In this illustration, the sheath 703 has been slid distally (i.e. towards the balloon expandable component) over the proximal taper of the balloon expandable component 704 until the distal end of the sheath is aligned with the distal end of the balloon. Cross section H-H in FIG. 7D shows the fully constrained or resheathed balloon expandable component 704 within the sheath 703 resuming the fully groomed profile provided prior to the initial inflation shown in cross section B-B in FIG. 7A.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A device to return an inflated balloon to a substantially low profile following deflation, comprising:
   an elongate catheter shaft comprising a proximal end and a distal end defining a longitudinal axis there between and a lumen extending between the proximal end and the distal end;
   an expandable member comprising an interior, an exterior, a proximal end, and a distal end, wherein the proximal end of the expandable member is coupled to the distal end of the elongate catheter shaft such that the interior of the expandable member is in communication with the lumen of the elongate catheter shaft, and wherein the expandable member is expandable from a collapsed state to an expanded state when pressurized;
   a stationary inner member comprising a proximal end and a distal end, wherein the distal end of the expandable member is positioned at the distal end of the stationary inner member;
   a catheter hub comprising a biasing member, wherein the catheter hub comprises an inflation port and is positioned at the proximal end of the stationary inner member;
   wherein the biasing member is slidably disposed within the catheter hub and wherein a distal end of the biasing member is positioned at the proximal end of the elongate catheter shaft.

2. The device of claim 1, wherein upon pressurizing the expandable member provides for a lateral motion in a distal direction of the elongate catheter shaft.

3. The device of claim 1, wherein upon depressurizing the expandable member provides for a lateral motion in a proximal direction of the elongate catheter shaft thereby providing at least partial collapse of the expandable member from the expanded state.

4. The device of claim 1, wherein the catheter hub comprises the inflation port in communication with the expandable member through the lumen of the elongate catheter shaft; wherein the inflation port is configured to be connected to an inflation device to pressurize and de-pressurize the expandable member.

5. The device of claim 1, wherein the biasing member is a piston that divides the catheter hub into a distal chamber and a proximal chamber, where the proximal chamber is in communication with the interior of the expandable member and the inflation port of the catheter hub.

6. The device of claim 5, wherein the proximal chamber of the catheter hub is configured to be pressurized to overcome the biasing member to dispose the biasing member in a distal position relative to the catheter hub.

7. The device of claim 1, wherein pressurization of the expandable member is achieved by application of pneumatic or hydraulic pressure.

8. The device of claim 1, wherein the biasing member further comprises a spring that disposes the biasing member in a proximal position relative to the catheter hub when the device is at or below atmospheric pressure.

9. The device of claim 1, where the stationary inner member comprises a wire, a tube, a coil, or a braid.

10. The device of claim 9, wherein the stationary inner member comprises nitinol (nickel titanium alloy), stainless steel, polyimide, aluminum, PEEK, or titanium.

11. The device of claim 1, wherein the elongate catheter shaft is configured and arranged to be slidable over the stationary inner member.

12. The device of claim 1, wherein the elongate catheter shaft comprises polyimide, polyether block amide (PEBA), braided polyimide, braided PEBA, stainless steel, nitinol, PEEK, aluminum, titanium, nylon, braided nylon, or polytetrafluoroethylene.

13. The device of claim 1, wherein the expandable member comprises a balloon.

14. The device of claim 13, wherein the balloon comprises nylon, PET, polyethylene, polyurethane, silicone rubber, or PEBA.

15. The device of claim 1, wherein the expandable member comprises a braided structure and linkages to provide for expansion of the expandable member.

16. The device of claim 1, wherein the biasing member comprises a spiral rail or groove that engages with the catheter hub via a linkage pin to allow for rotational movement of the biasing member with respect to the catheter hub when the device is in a pressurized state or a de-pressurized state.

17. The device of claim 16, wherein the rotational movement of the biasing member is transmitted to the proximal end of the expandable member via the elongate catheter shaft.

18. The device of claim 16, wherein the rotational movement of the biasing member provides for return of the expandable member to a substantially low profile upon transition of the expandable member to the de-pressurized state.

19. The device of claim 1, wherein the biasing mechanism comprises a longitudinal rail or groove that interacts with the catheter hub via a linkage pin such that the biasing mechanism does not rotate with respect to the catheter hub when the apparatus is pressurized or de-pressurized via the catheter hub.

20. The device of claim 1, wherein the expandable member comprises multi-pleat folds that are arranged in a substantially longitudinal orientation after the expandable member is de-pressurized or deflated.

21. The device of claim 1, wherein the expandable member comprises multi-pleat folds that are arranged in a substantially spiral or twisted orientation after the expandable member is de-pressurized or deflated.

22. The device of claim 21, wherein the substantially spiral or twisted multi-pleat folds of the expandable member are induced by rotating the elongate catheter shaft relative to the stationary inner member.

23. The device of claim 21, wherein retention of the substantially spiral or twisted multi-pleat folds of the expandable member is by preventing the elongate catheter shaft from rotating in a direction opposite the expandable member.

24. The device of claim 21, wherein the substantially spiral or twisted multi-pleat folds of the expandable member are induced by a folding, a pleating, or a wrapping process.

25. The device of claim 21, wherein the substantially spiral or twisted pleats of the expandable member are induced by a folding, pleating, or wrapping process combined with a rotation of the elongate catheter shaft.

26. The device of claim 1, wherein an inner wall of the elongate catheter shaft comprises ribs or bumps or features that constrain the stationary inner member within the lumen of the elongate catheter shaft to prevent or minimize the inner member from assuming a wavy condition or buckling within the lumen of the elongate catheter shaft.

27. The device of claim 1, wherein the stationary inner member comprises ribs, bumps or features that constrain the inner member within the lumen of the elongate catheter shaft and prevent or minimize the inner member from assuming a wavy condition or buckling within the lumen of the elongate catheter shaft.

28. The device of claim 1, wherein the elongate catheter shaft, expandable member, stationary inner member, or catheter hub comprises a marker or multiple markers.

29. The device of claim 28, wherein the marker or markers are radiopaque.

30. The device of claim 28, wherein the marker or markers are macroscopically visible.

* * * * *